United States Patent
Adami et al.

(10) Patent No.: US 9,075,029 B2
(45) Date of Patent: Jul. 7, 2015

(54) SYSTEM AND METHOD FOR AUTOMATICALLY ADJUSTING GAS SENSOR SETTINGS AND PARAMETERS

(75) Inventors: Fatos Adami, Stallings, NC (US); Nicholas Anthony DeBlasio, Monroe, NC (US); Byron Eugene McLendon, Matthews, NC (US); Stephen Edwin Mealy, Jr., Indian Trail, NC (US); Keli Chalfant Merkel, Waxhaw, NC (US); Edward Russell Propst, Jr., Monroe, NC (US)

(73) Assignee: Scott Technologies, Inc., Boca Raton, FL (US)

( * ) Notice: Subject to any disclaimer, the term of this patent is extended or adjusted under 35 U.S.C. 154(b) by 1122 days.

(21) Appl. No.: 13/018,039

(22) Filed: Jan. 31, 2011

(65) Prior Publication Data
US 2012/0192623 A1    Aug. 2, 2012

(51) Int. Cl.
*G01N 33/00* (2006.01)
*G01D 18/00* (2006.01)
*G01D 4/00* (2006.01)

(52) U.S. Cl.
CPC .......... *G01N 33/0031* (2013.01); *G01D 18/002* (2013.01); *G01D 4/004* (2013.01); *G01N 33/007* (2013.01); *G01N 33/0006* (2013.01)

(58) Field of Classification Search
CPC ..... G01N 33/007; G01D 18/00; G01D 4/004; G01D 21/02
USPC ....................................................... 702/107
See application file for complete search history.

(56) References Cited

U.S. PATENT DOCUMENTS

| | | | | | |
|---|---|---|---|---|---|
| 4,476,706 | A | * | 10/1984 | Hadden et al. | 73/1.07 |
| 4,875,031 | A | * | 10/1989 | Filippi et al. | 340/605 |
| 4,897,884 | A | * | 1/1990 | Heller | 398/109 |
| 5,025,653 | A | * | 6/1991 | Schuldt | 73/23.2 |
| 5,253,511 | A | * | 10/1993 | Jaramillo et al. | 73/1.88 |
| 6,005,500 | A | * | 12/1999 | Gaboury et al. | 341/143 |
| 6,229,469 | B1 | | 5/2001 | Gaudet | |
| 6,428,665 | B1 | | 8/2002 | Ilic et al. | |
| 6,611,208 | B1 | * | 8/2003 | Ketler | 340/632 |
| 6,794,991 | B2 | * | 9/2004 | Dungan | 340/632 |
| 7,223,014 | B2 | * | 5/2007 | Lojen | 374/120 |
| 2005/0280408 | A1 | * | 12/2005 | Wobschall | 324/115 |

(Continued)

*Primary Examiner* — Lisa Caputo
*Assistant Examiner* — Punam Roy
(74) *Attorney, Agent, or Firm* — Wyatt B. Pratt

(57) ABSTRACT

A system and method are disclosed including an automatic sensor excitation voltage adjustment feature, a multi-range concentration feature, and a single calibration feature. The automatic sensor excitation voltage adjustment feature may include a transmitter having an associated microprocessor that provides an initial voltage to an associated sensor. The sensor may include a microprocessor, and as the voltage changes a correction signal may be relayed from the sensor microprocessor to the transmitter microprocessor. The correction signal may be used by the transmitter microprocessor to adjust the voltage applied to the sensor. The multi-range concentration sensor feature may include an amplifier associated with the sensor/microprocessor to create gain settings used to optimize sensor resolution by changing a gain value associated with the sensor. This, in turn, enables a single sensor to be used for a variety of different concentration ranges, as desired by a user. The single calibration feature enables a sensor to be calibrated at a single gas concentration value, and thereafter be used for a variety of different concentration range applications. Other embodiments are described and claimed.

10 Claims, 11 Drawing Sheets

(56) References Cited

U.S. PATENT DOCUMENTS

| | | |
|---|---|---|
| 2006/0123931 A1 | 6/2006 | Wareham et al. |
| 2008/0242962 A1* | 10/2008 | Roesicke et al. ............. 600/347 |
| 2009/0242427 A1 | 10/2009 | Muroguchi et al. |
| 2009/0302856 A1* | 12/2009 | Babel et al. ................... 324/438 |
| 2014/0238101 A1* | 8/2014 | Mealy et al. ................... 73/1.06 |

* cited by examiner

SYSTEM AND METHOD FOR AUTOMATICALLY ADJUSTING GAS SENSOR SETTINGS AND PARAMETERS

FIELD OF THE DISCLOSURE

The present disclosure relates to gas detection systems in general, and more particularly to a gas detection system platform in which a plurality of different sensor types can be used with a single transmitter design, and in which the plurality of different sensor types can be automatically recognized, adjusted, calibrated, and monitored with reduced user input.

BACKGROUND OF THE DISCLOSURE

Environmental sensing systems may include a variety of sensors to determine the presence and concentrations of hazardous (i.e., combustible) and/or toxic gases in industrial and other workspaces. Depending on the environment, it may be desirable to provide sensing information for a wide variety of different gas types and concentrations. Thus, a typical system can include a large number of different types of sensors, where each type of sensor is adept at sensing a particular gas in a desired concentration range.

In order for a particular sensor to detect a desired gas in a particular concentration range, and to transmit that information in a form readily understood by a remote transmitter, the sensor's output signals must be properly conditioned. Currently, sensor signal conditioning is accomplished by using discreet components (i.e. resistors, capacitors, operational amplifiers, etc.) to filter and amplify a specific sensor's output prior to performing a conversion to the digital domain for further processing. In one example, signals from electrochemical sensors are typically conditioned using the well-known potentiostat circuit. The drawback to using discrete components, however, is that the arrangement of such components is often specific to a particular type of sensor, and also to a particular gas being sensed as well as a desired concentration range. Thus, developing conditioning circuits for a wide range of gases and ranges requires changing the values of these components to achieve optimum analogue signal conditioning. This, in turn, requires a wide variety of conditioning circuits to cover ranges of potential interest. As a result, a large number of sensors of differing types, and of differing concentration range capacities, must be manufactured and stocked to meet the associated wide variety of field applications. Moreover, most sensors operate in combination with an associated transmitter unit. Due to the specialized nature of the described sensors, such transmitters often only work with a single sensor type. As such, current systems require that a similarly large number of different transmitters also must be manufactured and stocked.

In addition, when current remote transmitter and sensors are installed and/or replaced, they must be individually adjusted to ensure they are appropriately calibrated, and also to ensure that they are in proper working condition. Currently, for remote transmitter and sensor applications this adjustment/verification process is a two-person effort in which one person must stand at the sensor location reading a digital voltage meter, and a second person must at the transmitter adjusting a manual potentiometer to achieve a desired output voltage for supplying the sensor. When this operation takes placed in a hazardous area, it can require that the area be declassified so that the transmitter can be opened to access the manual potentiometer. Much the same is true for integral transmitter and sensor applications, in which one person must read a digital voltage meter and adjust a manual potentiometer at the transmitter to achieve a desired output voltage for supplying the sensor. This can also undesirably involve declassifying the associated hazardous area to open the transmitter to access the manual potentiometer.

It will further be appreciated that sensors undergo sensitivity losses over time. Present systems are not able to provide automatic recognition and adjustment of sensors to compensate for such losses in sensitivity. This, in turn, can lead to premature disposal of sensors that drop below a desired sensitivity threshold. Since such sensors ostensibly would continue to function desirably if their loss in sensitivity could be compensated for, current systems produce unnecessary waste.

Accordingly, there is a need for an improved environmental sensing system that: enables a single transmitter to recognize and accept a plurality of different sensor types, automatically adjusts installed sensors to reduce or eliminate the need for manual adjustment, automatically calibrates sensors to enable a single sensor to accommodate a variety of different sensing ranges, enables a sensor to be calibrated at a single value and then be used at a variety of values, and enables automatic adjustments to extend sensor lifetime.

SUMMARY OF THE DISCLOSURE

An environmental sensing system solving one or more of the aforementioned problems is disclosed. Specifically, a system is disclosed including: (1) an automatic sensor excitation voltage adjustment feature, (2) a multi-range concentration feature, and (3) a single calibration feature. The automatic sensor excitation voltage adjustment feature may include a transmitter having an associated microprocessor that provides an initial voltage to an associated sensor. The sensor also may have an associated microprocessor, and as the voltage changes, a correction signal may be relayed from the sensor microprocessor to the transmitter microprocessor. The correction signal may be used by the transmitter microprocessor to adjust the voltage being applied to the sensor to a desired value. The multi-range concentration sensor feature may include an amplifier associated with the sensor/microprocessor to create gain settings which can then be used to optimize sensor resolution by changing a gain value associated with the sensor. This, in turn, may enable a single sensor to be used for a variety of different concentration ranges, as desired by a user. The single calibration feature enables a sensor to be calibrated at a single gas concentration value, and thereafter be used for a variety of different concentration range applications.

A system is disclosed for recognizing and adjusting sensor voltage by using digital potentiometers, without human intervention and without the need to declassify a hazardous area. The system may include a gas detector/transmitter power supply circuit comprising an adjustable power supply with a pair of digital potentiometers. One potentiometer can be used for coarse voltage adjustment, and the second potentiometer can be used for fine voltage adjustment. An output voltage from this power supply circuit is referred to as $V_{adjust}$, and is used to power a sensor associated with the transmitter. This arrangement enables a single transmitter design to be used with a multiplicity of different sensor types and ranges, as the power supply circuit is able to automatically adjust the sensor excitation voltage ($V_{adjust}$) to a specific value associated with the particular sensor being used. It can also compensate for voltage variations due to environmental changes and voltage drop in the intervening cable.

The disclosed system enables sensors to be replaced under power, without declassifying the associated area. In addition, the disclosed system can reduce the overall cost of ownership by enabling replacement of only the sensor kernel at sensor end of life, as opposed to current systems which require replacement of an entire sensor unit.

A system is disclosed for detecting the presence of a gas, comprising a transmitter portion, a sensor portion, and a variable voltage supply associated with the transmitter portion and the sensor portion. The transmitter portion may receive information from the sensor portion regarding a received voltage. The transmitter portion may also adjust the supplied voltage in response to the information received from the sensor portion.

A method is disclosed for adjusting sensor excitation voltage. The method may include providing, at a transmitter portion, an operating voltage to a sensor portion, receiving, at the transmitter, a signal from the sensor portion indicating a voltage required for operation of the sensor portion, and adjusting, at the transmitter, the operating voltage provided to the sensor portion.

A universal gas sensor/transmitter unit is disclosed. The unit may include a sensor portion including a sensor kernel and a processor configured to read a received excitation voltage. The unit may also include a transmitter portion having a recess configured to engage the external surface geometry of the sensor. The transmitter may include a transmitter processor and at least one power supply circuit for providing adjustable power to the sensor when the enclosure is engaged with a recess of the transmitter. The adjustable power supply circuit may include at least one potentiometer controllable by the processor to adjust a power supplied to the sensor portion.

A method for calibrating a sensor is disclosed. The method may include setting an original zero offset and a spanning of a sensor at a first gain setting; obtaining a zero offset at a second gain setting; obtaining a ratio of the original zero offset to the zero offset at the second gain setting; and scaling a calibration factor by the ratio to enable operation of the sensor in an operating range associated with the second gain setting.

A method for providing replacement guidance for a sensor is also disclosed. The method may include determining a reduction of sensitivity for a sensor, trending said reduction of sensitivity over time, and adjusting a gain parameter associated with said sensor to compensate for said reduction of sensitivity.

A method for adjusting an operating range for a sensor is disclosed. The method may include providing an amplifier associated with said sensor, providing a table of gain settings for said amplifier, and selecting a gain setting from said table to optimize a resolution in an analog to digital converter associated with the sensor. Selecting a gain setting may adjust the sensor to one of a plurality of pre-determined operating ranges.

BRIEF DESCRIPTION OF THE DRAWINGS

By way of example, a specific embodiment of the disclosed device will now be described, with reference to the accompanying drawings, in which.

DETAILED DESCRIPTION

Figure 1:
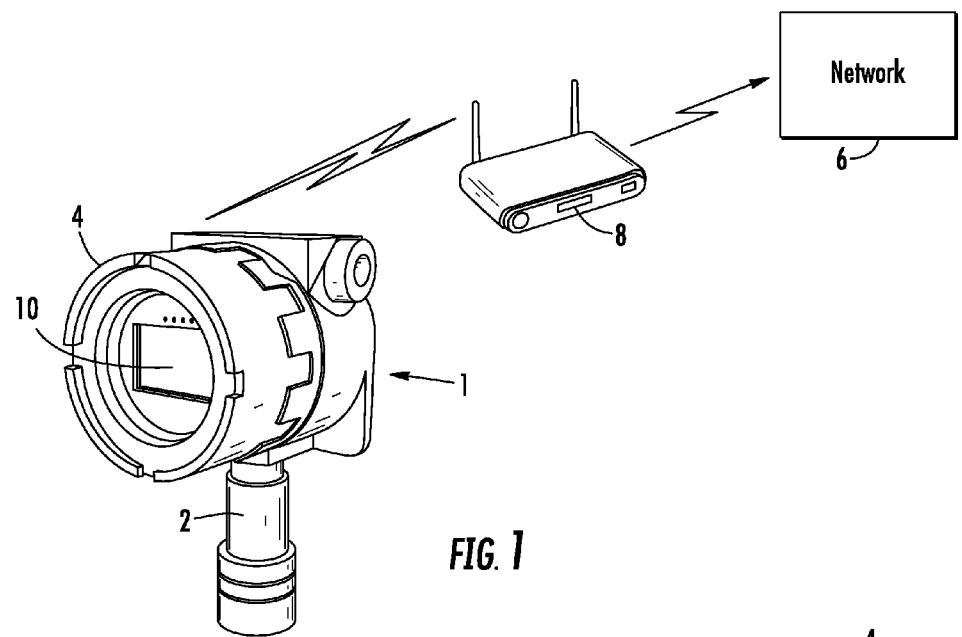
FIG. 1 is an illustration of an exemplary transmitter/sensor combination.

The disclosed system and method takes advantage of advances in microelectronics and performs final signal conditioning of a sensor using amplification built into microprocessors. This amplification can be software controlled to be arranged in either a differential or additive mode. Additionally, the level of gain can be adjusted in discrete levels, thus allows a wide range of input signals to be accommodated in a single circuit without resorting to changing in discrete components.

Three applications are realizable. First, a single sensor can be built for a specific gas, and the range of the sensor can be optimized for a particular application. For example, one sensor can be provided in either a 0-10 ppm or 0-100 ppm range simply by changing software parameters. Secondly, variations in sensor sensitivity can be accommodated over a wider range, leading to greater manufacturing throughput. Previously, sensor kernels had to be screened to ensure their sensitivity could be accommodated by a particular fixed circuit design. Now a wider variability in sensitivity can be utilized, leading to less manufacturing waste. Lastly, as sensors are subjected to normal use, their sensitivities degrade. With prior designs, once the sensor's sensitivity had degraded to the point the fixed circuit cannot compensate for this degradation, the sensor had reached the end of its useful life. The current system and method can be used to compensate for sensor sensitivity degradation beyond the traditional limit by adjusting gain upward. This has the advantage of reducing life cycle cost for a gas detector by reducing the total number of sensor replacements.

As previously noted, current systems utilize fixed circuit designs for each range of a target gas. In practice, sensors need to be calibrated on a recurring basis to ensure accuracy. Calibration is performed at 2 points: one with no gas present (zero), and one point within the sensor's range (span), where the span is typically 25-75% full scale. In an installation with sensors of various ranges, this requires the presence of multiple calibration gasses at different concentrations.

With the disclosed system and method, the calibration variables are scaled to different ranges within the sensor. This enables calibration using one concentration of calibration gas and then adjusting the range of the sensor for the particular application. This has the advantage of enabling calibration of different range sensors using one common calibration gas. As will be appreciated, this reduces the number of different concentration calibration gasses required, and/or it eliminates the need to use a gas concentration that is more widely available than another for a specialized application.

A gas sensor/transmitter combination is disclosed that recognizes and adjusts sensor voltage by using digital potentiometers, without human intervention and without declassifying a hazardous area. A gas sensor/transmitter power supply circuit includes an adjustable power supply with two digital potentiometers. One potentiometer is for coarse voltage adjustment and the second potentiometer is for fine voltage adjustment. The output voltage of this power supply circuit is called $V_{adjust}$ and aids in powering the sensor associated with the transmitter.

Referring now to FIG. 1, a transmitter/sensor combination 1 is shown comprising a sensor portion 2 and a transmitter portion 4. The transmitter portion 4 may be configured to transmit information received from the sensor portion 2 to a wireless network 6 via a wireless link 8. The wireless link 8 can be any of a variety of protocols, including Modbus, HART, ISA 100.11a, wireless HART, Foundation fieldbus, Profibus, and the like. The wireless network 6 may distribute information received from the transmitter portion 4 to one or more local or remote alarms, and one or more local or remote monitoring stations via intranet, Internet, Wi-Fi, or other network arrangement. It will be appreciated that although FIG. 1 illustrates a wireless connection to network 6, that the invention is not so limited. Thus, the connection could be hard wired.

As will be understood, the primary purpose of the sensor portion 2 is to sense a target gas and provide signals representative of the concentration of that gas to the transmitter portion 4. The primary purpose of the transmitter portion 4 is to collect information from the sensor portion 2 and to transfer that data upstream. Upstream devices may include controllers, gateways, converters and similar devices.

Figure 2:
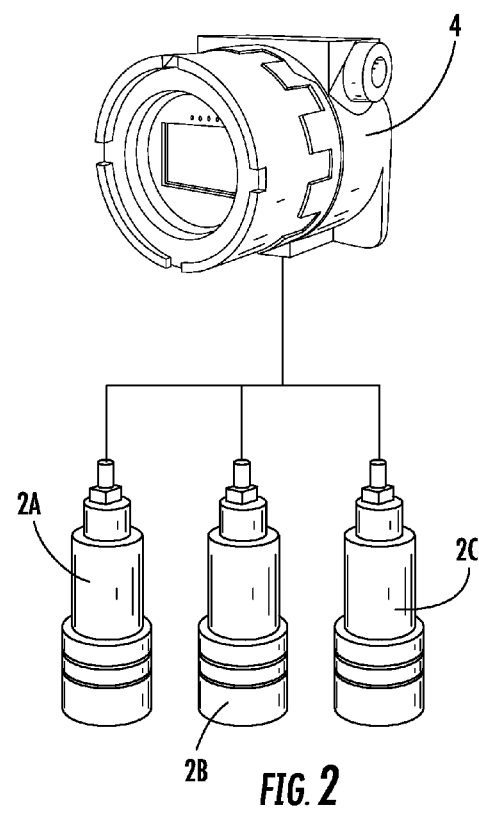
FIG. 2 is an illustration of the transmitter portion of FIG. 1 associated with a plurality of different sensor portion types.

In addition to remote transmission of sensor data, the transmitter portion may include a local display 10 for providing local indication of sensor operation. In some embodiments, the transmitter portion 4 may be configured to accept a plurality of sensor heads to provide an expanded area coverage. FIG. 2 shows a transmitter portion 4 hardwired to a plurality of sensor portions 2A-2C representing a plurality of different sensor types that can be used with the transmitter portion 4. Indeed, although the description will proceed in relation to a transmitter portion 4 associated with a single sensor portion 2, it will be appreciated that the transmitter portion 4 may be associated with, and accept signals from, a plurality of sensor portions 2A-2C at once.

As will be appreciated, the sensor portion 2 (or sensor portions, where multiple sensors are used with a single transmitter) may be any of a variety of known sensor types, a non-limiting exemplary listing of such types including an IR gas sensor, a catalytic bead detector, an electro-chemical sensor, a photo-ionization detector, and a metal-oxide sensor.

In practical application, particular sensor portions 2 may be used to detect a wide variety of toxic gases, an exemplary listing of which includes, but is not limited to, Ammonia, Arsine, Boron Trichloride, Boron Trifluoride, Bromine, Carbon Dioxide, Carbon Monoxide, Chlorine, Chlorine Dioxide, Diborane, Fluorine, Germane, Hydrogen, Hydrogen Bromide, Hydrogen Chloride, Hydrogen Cyanide, Hydrogen Fluoride, Hydrogen Sulfide, Methanol, Methyl Mercaptan, Methyl Iodide, Nitric Oxide, Nitrogen Dioxide, Nitrogen Trifluoride, Oxygen, Ozone, Phosphine, Silane, Silicon Tetrafluoride, Sulfur Dioxide, TEOS, and Tungsten Hexafluoride.

In addition, particular sensor portions 2 may be used to detect a wide variety of combustible gases, a non-limiting exemplary listing of which includes Acetone, Benzene, Butadiene, Butane, Ethane, Ethanol, Ethylene, Hexane, Hydrogen, Isobutanol, Isopropyl Alcohol, Methane, Methanol, Methyl Ethyl Ketone (MEK), Pentane, Propane, Propylene, Toluene, and Xylene.

Figure 3:
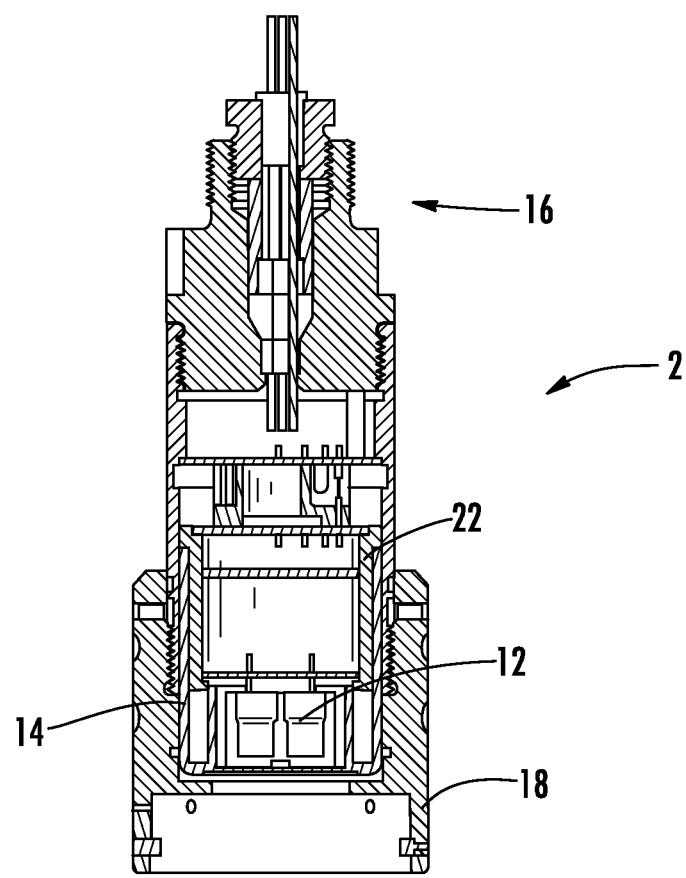
FIG. 3 is a cross section view of an exemplary sensor portion assembly for use with the transmitter portion of FIG. 1.

A benefit of the disclosed arrangement is that a single transmitter portion 4 may quickly accept any of a variety of sensor portions 2. Thus, as shown in FIG. 3, the sensor portion 2 may include internal sensing components such as a sensor kernel 12, mounted within an upper sensor enclosure 22. And although different sensor portions 2 may include different sensor kernels 12, as well as additional processing components, all of the different sensor kernels 12 will be fit within upper and lower sensor enclosures 22, 14, thus allowing the sensor portion 2 to be of a single size and shape for all applications.

An end cap 18 may be arranged to allow simple installation of a particular sensor kernel 12 and associated components. This can make it possible to replace a sensor kernel 12 without requiring the remaining components of the sensor portion 12 to be replaced.

Thus arranged, to engage the sensor portion 2 with the transmitter portion 4, the upper region 16 of the sensor portion 2 is inserted into a recess (not shown) in the transmitter portion 4, and the end cap 18 of the sensor portion 2 engages the recess and locks the sensor portion 2 to the transmitter portion 4. The end cap 18 may have one or more recesses or other geometry suitable for receiving an o-ring, gasket or the like to seal the sensor portion 2 to the transmitter portion 4. This sealing arrangement protects the internal sensor and transmitter components from potentially harsh exterior environments. A lower sensor enclosure 14 can include self-aligning features (e.g., keyed interaction with the transmitter) that can further facilitate quick installation and replacement of sensor portions 2. Retaining features, such as external threads and the like, can also be provided to ensure firm engagement of the sensor portion 2 with the transmitter portion 4.

Figure 4:
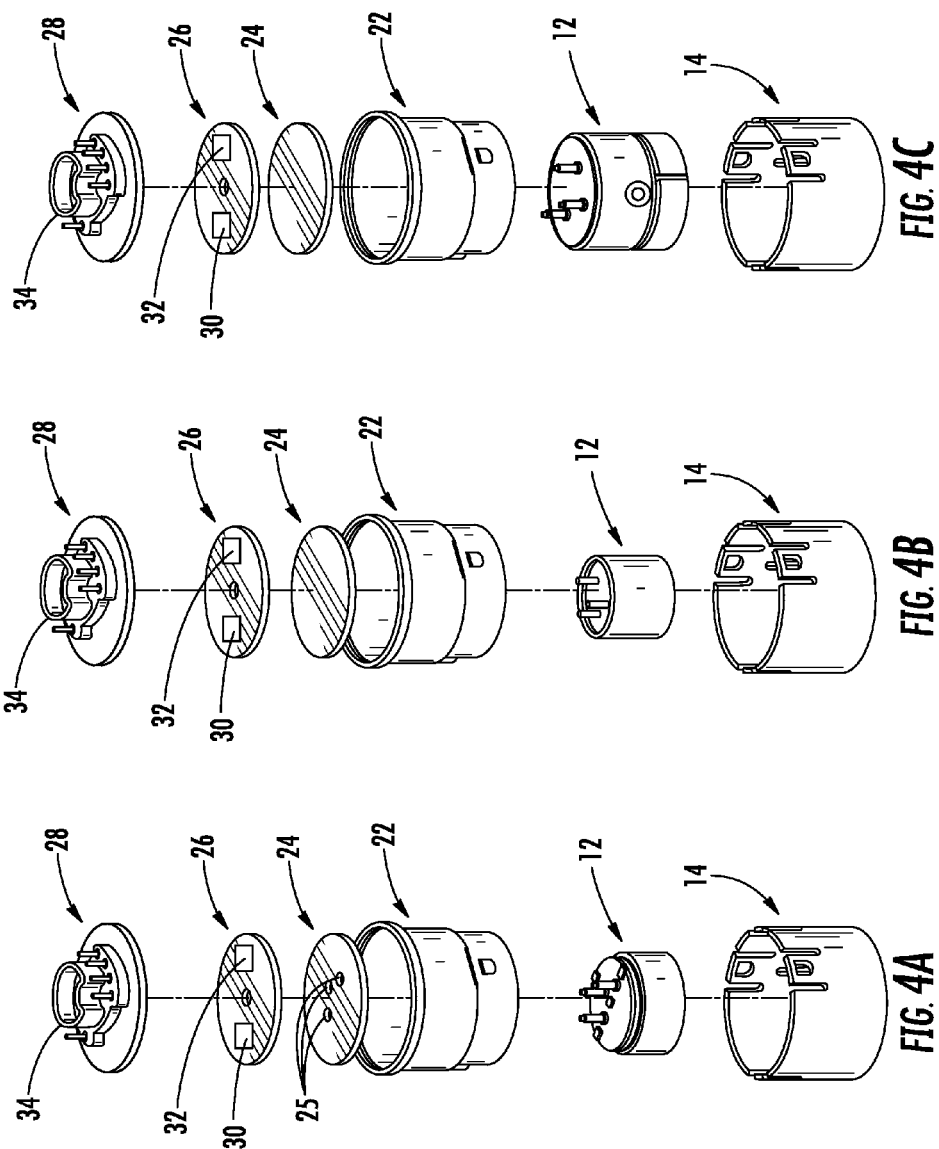
FIGS. 4A-4C are exploded views of respective sensor portion assemblies for use with the transmitter portion of FIG. 1.

FIGS. 4A-4C show a plurality of sensor portions 2 used for sensing different gas types. As can be seen, each of the sensor portions 2 includes a lower sensor enclosure 14, an upper sensor enclosure 22, a sensor kernel 12, a contact board 24, a sensor printed circuit board (PCB) 26, and an interface PCB 28. As can be seen, the sensor kernel 12 has a different size/geometry for each of the different sensor portions 2. Such differences can be accommodated by the upper sensor enclosure 22 which can have an internal geometry configured to receive the specific sensor kernel 12, but which has a common external configuration so that it can be received by the lower sensor enclosure 14. These differences also may be accommodated by the contact board 24, which may include receptacles 25 (see FIG. 4A) to plug in the specific sensor kernel 12. This allows the sensor portion 2 to be of a single size and shape for all applications.

As can be seen, a variety of different sized/shaped sensor kernels can be accommodated without impacting the external arrangement of the sensor portion 2. Thus, each of the sensor portions 2 of FIGS. 4A-C can fit to the transmitter portion 4 in exactly the same physical manner.

The sensor PCB 26 may be unique to each sensor kernel 12, and as such it may include a sensor processor 30, as well as a conditioning circuit 32 that performs conditioning of the signals received from the sensor kernel 12. For example, the conditioning components 32 may convert the signal from the sensor kernel in µA per ppm to a voltage level useable by the sensor processor's analog to digital converter. The interface PCB 28 provides an interface between the sensor PCB 26 and the transmitter portion 4. The interface PCB 28 may include a pin arrangement 34 common to all sensor portions 2 that is configured to be received by the transmitter portion 4.

As arranged, in one embodiment the sensor portion 2 may constantly measure a local target gas concentration, supply voltage, and ambient temperature and report a temperature compensated gas concentration, when requested, to the transmitter portion 4.

Figure 5:
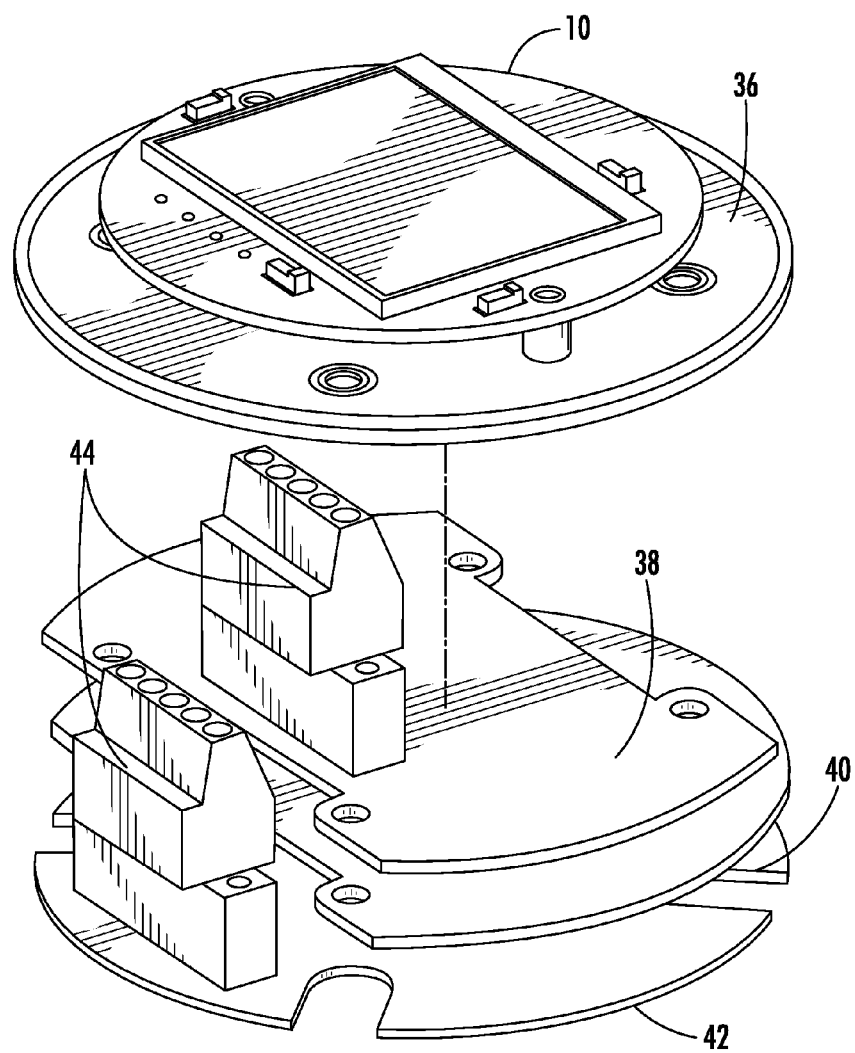
FIG. 5 is an exploded view of the transmitter portion of FIG. 1.

FIG. 5 shows the internal components of the transmitter portion 4, which may include a display 10, processor board 36, relay/network board 38, power supply board 40, and intrinsic safety (IS) barrier 42. One or more plug-in blocks 44 may also be included for providing a variety of connectivity functions for the transmitter portion 4. The plug-in blocks 44 may be used to provide power, relays, remote acknowledge, communications and sensor connections.

Figure 6:
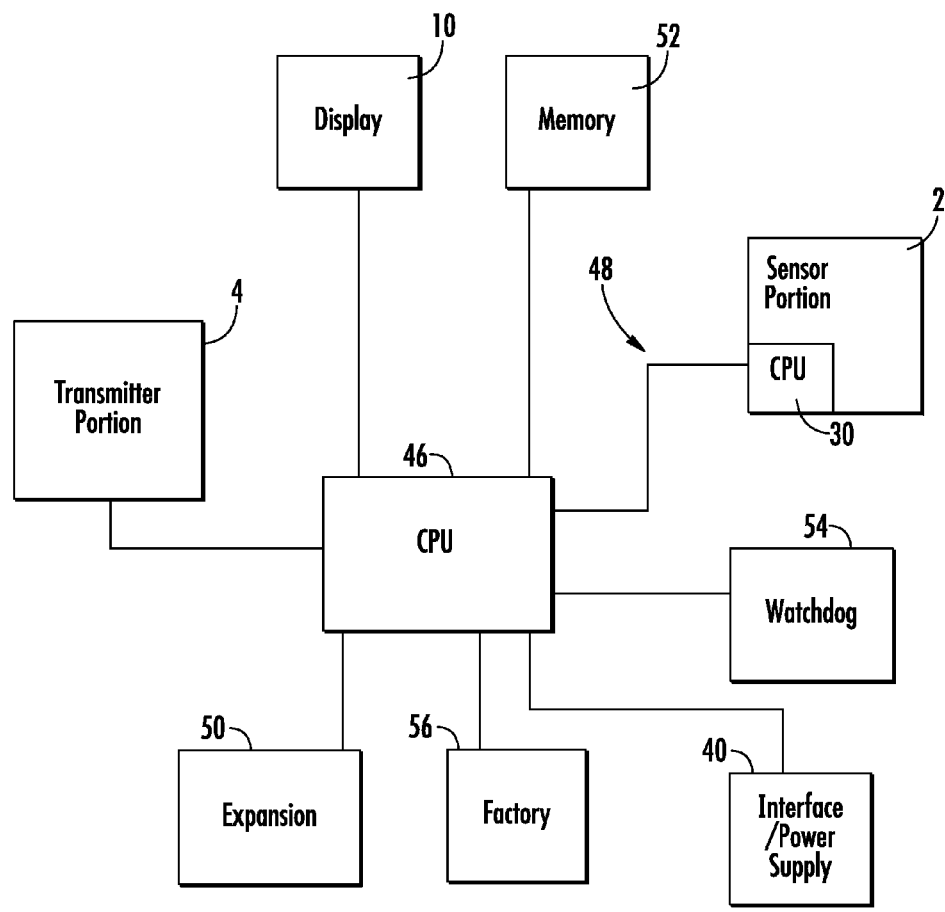
FIG. 6 is a system diagram of the transmitter/sensor combination of FIG. 1.

FIG. 6 shows a logical arrangement of an exemplary transmitter/sensor combination 1 in accordance with one or more embodiments. In the illustrated embodiment, the transmitter portion 4 comprises a processor 46 that connects to the sensor portion 2 via digital communication 48, and it relays the output of the sensor portion 2 through a variety of communications means. A display 10 is provided to permit local monitoring of data as well as setting parameters and setting system parameters associated with process changes and calibration. An expansion port 50 is provided to enable methods of communication beyond the 4 to 20 milliamp signal and MODBUS. Memory 52 is provided to allow a history of process data, calibration data and expanded user information. Watchdog circuits 54 are provided to assure enhanced reliability. One or more additional circuits 56 can be provided for factory use to program and test the device during production. Interface/power supply 40 provides power to the transmitter portion 4 and the sensor portion 2.

The inputs to the transmitter portion 4 can be HART, Serial communication from a host, serial communication from sensors, I$^2$C communication from on-board and off-board devices, SPI communication from on-board and off-board devices and contact closures from magnetic switches located on the display 10. The outputs from the transmitter portion 4 include LEDs on the display 10, LCD on the display 10, alarm relays, 4-20 milliamp current loops, MODBUS communication with external hosts, I$^2$C communication to on-board and off-board devices, SPI communications to on-board and off-board devices, power for multiple sensors, and optional serial communications modules for external hosts.

Figure 7:
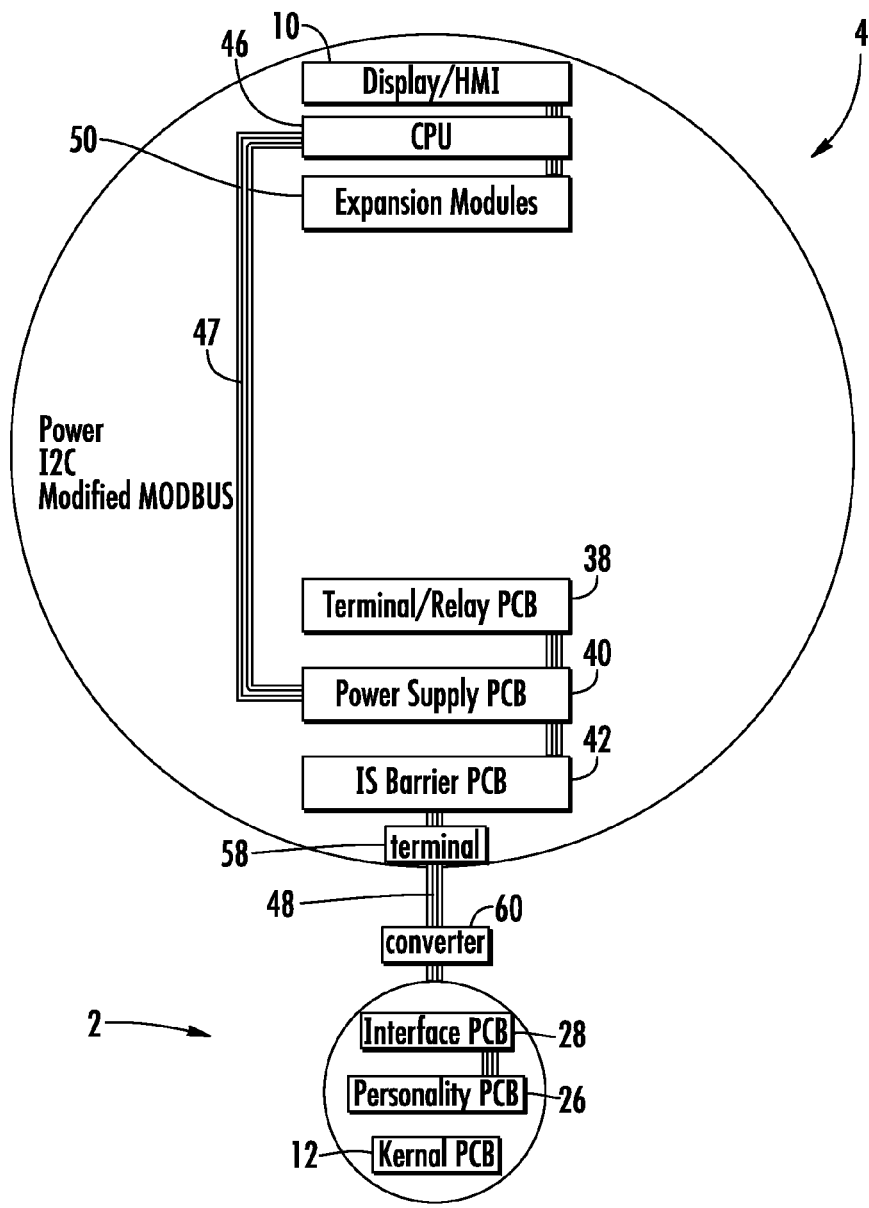
FIG. 7 is system board level diagram of the transmitter/sensor combination of FIG. 1.

FIG. 7 shows a board level diagram illustrating the interconnection between the transmitter portion 4 and the sensor portion 2. The transmitter portion 4 may include display 10, processor 46, expansion modules 50, terminal/relay board 38, power supply board 40, and IS barrier 42. A connection 47 is provided between the processor 46 and the power supply board 40.

The display 10 generally provides human interfaces, graphical LCD, magnetic switch inputs, and alarm status LEDs. The processor 46 controls functions of the transmitter and includes non-volatile memory 52. The expansion modules may include capabilities for wired or wireless communications as previously described. Terminal/relay board 38 may provide standard connections including power, relay, 4 to 20 mA, RS485 MODBUS, and remote acknowledge. The power supply board 40 may convert 10-30 V DC to 3.3V, 12V, may provide adjustable 2-9V sensor voltage, and may generate 4-20 mA loops. The IS barrier 42 may provide intrinsically safe connections to the sensor portion 2.

The transmitter portion 4 may further include a terminal 58 to provide a connection to the sensor portion 2. The terminal 58 may connect to digital communications 48 which itself can connect to a converter 60 for converting signals between RS485 and TTL levels. The process loop 48 connects to the interface PCB 28 of the sensor portion 2. As previously described, the interface PCB 28 connects to sensor PCB 26 and kernel 12. The sensor PCB 26 can include a sensor processor 30 and associated circuitry for providing sensor control, calculating gas concentrations, and performing temperature compensation and linearization.

Figure 8:
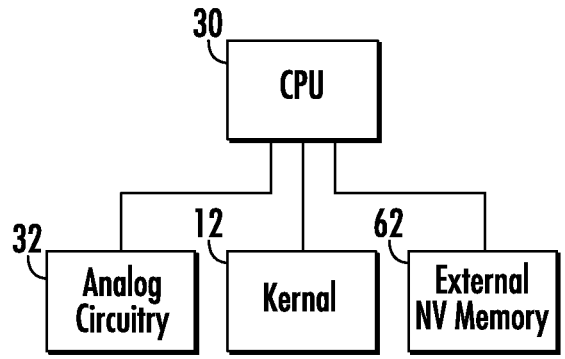
FIG. 8 is a block diagram for the sensor portion of FIG. 1.

FIG. 8 shows an exemplary block diagram for the sensor portion 2. When requested by the transmitter processor 46, the sensor portion 2 provides a digital output in response to a sensed gas input. The sensor portion 2 is connected to the transmitter via a cable 48. The transmitter portion 4 provides intrinsically safe power to the sensor portion 2, 3.3V and $V_{adjust}$, ground, and two IS communications signals. In general, the sensor portion 2 comprises a processor 30 in communication with conditioning circuitry 32, kernel 12 and memory 62. The memory 62 may include a variety of sensor specific information, including an excitation voltage value for the particular sensor with which the memory 62 is associated. In addition, the memory 62 may serve a data logging function, recording the sensor's historical exposure(s) to a target gas in order to develop a lifetime estimate for the sensor portion 2. The memory 62 may also store date/time and other significant events associated with the sensor portion 2.

In one embodiment, the sensor processor 30 may communicate with the transmitter processor 46 in a master/slave arrangement where the sensor is the slave. The sensor processor 30 may include as a peripheral an analog to digital converter (ADC) and 2.5V reference for converting analog kernel voltages representing gas concentration to their digital equivalent.

As will be appreciated, different types of sensors kernels are used to detect different types of target gases. The different types of sensor kernels generate an analog output as either a current, a voltage or a bridge output. The amplitudes of these signals across full scale also vary. The input of the sensor processor A/D 30 requires a reference voltage input from 0 to 2.5V. The individual sensor PCBs 26 for each type of sensor kernel 12 can provides conversion, amplification, filtering, and biasing, depending on the need of a particular sensor kernel.

Non-volatile memory 62 can be provided for storage of sensor parameters and other variables that need to be sustained during the loss of power. Some parameters are used locally by the sensor processor 30, but the majority are used by the transmitter processor 46.

The sensor interface PCB 28 may provide connection to the transmitter portion 4 is via an 8 pin connector 34 (FIGS. 3A-3C). A variety of signals may be accommodated in the connector 34, including ground, 3.3V, $V_{adjust}$, transmit (TX), receive (RX), DIR, and the like.

Figure 9:
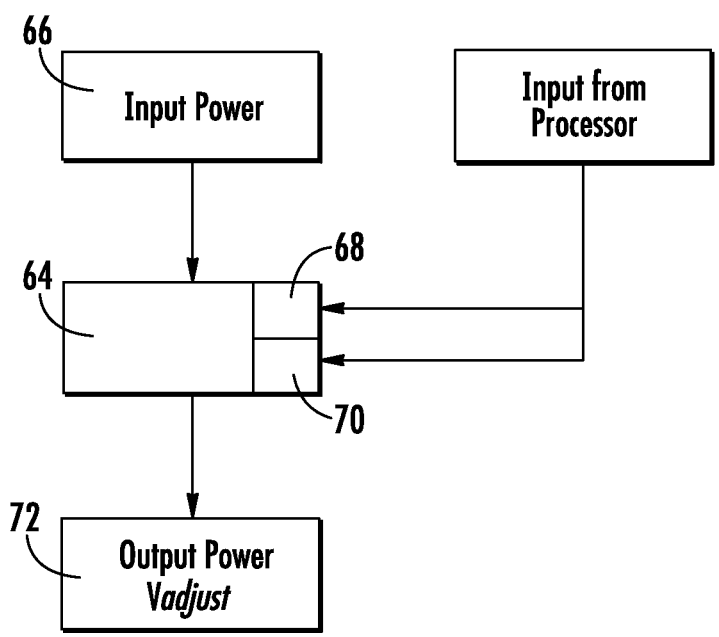
FIG. 9 is a block diagram of an exemplary power supply arrangement for the transmitter/sensor combination of FIG. 1.

Referring now to FIG. 9, a block diagram is shown for an adjustable power supply circuit 64 for the transmitter/sensor combination 1. The adjustable power supply circuit 64 may use an input voltage 66 of 10 to 30 VDC, and includes a step-down (buck) switching regulator with an adjustable output voltage ~2V to 9 VDC. Specifically, the adjustable power supply circuit 64 includes an adjustable power supply with two digital potentiometers 68, 70. One potentiometer 68 is for coarse voltage adjustment and the second potentiometer 70 is for fine voltage adjustment. As will be appreciated, output power 72 is adjusted by adjusting the potentiometers, and is provided to the sensor portion 2 accordingly.

Figure 10:
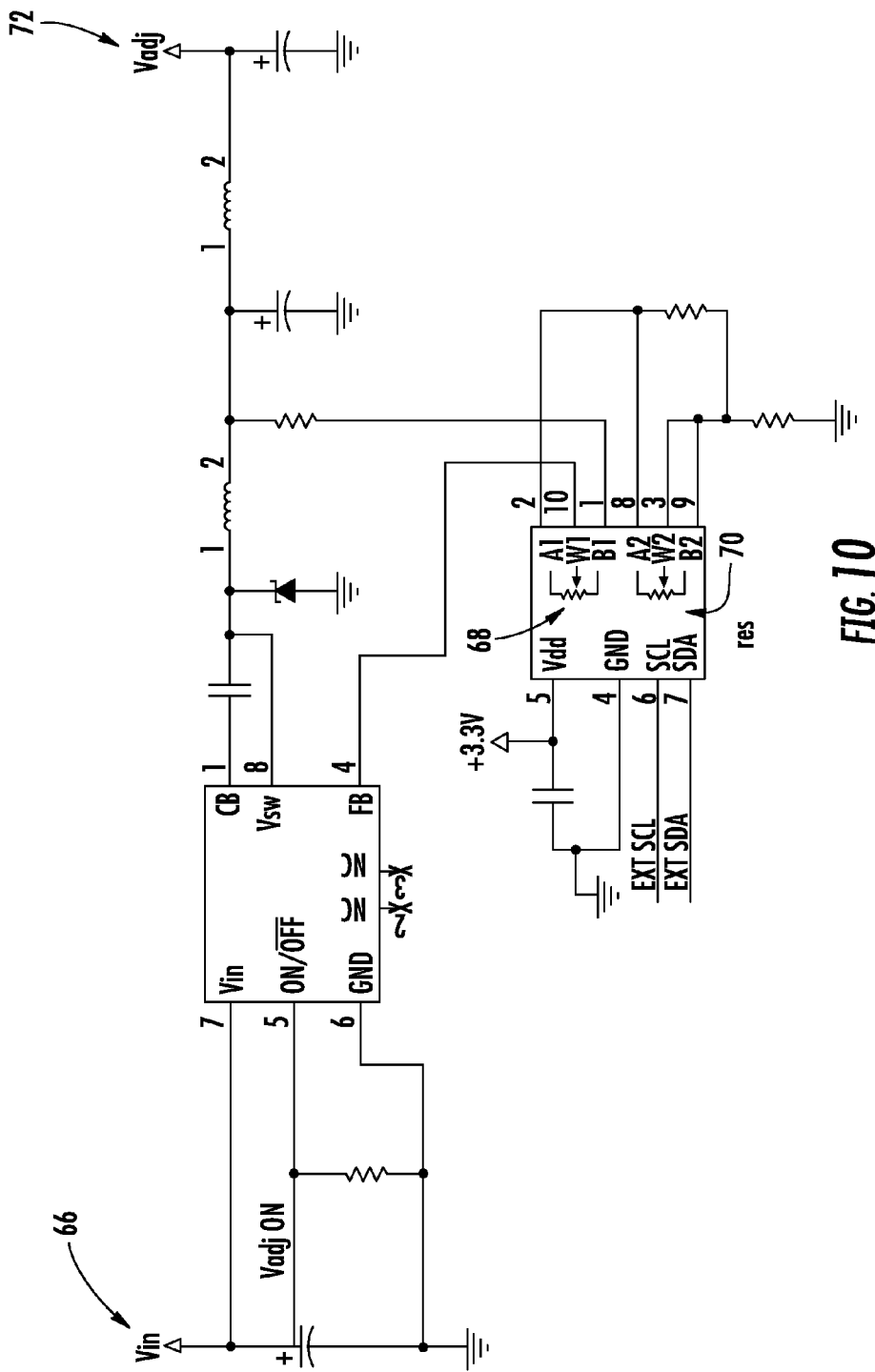
FIG. 10 is a circuit diagram of an exemplary adjustable power supply for use with the transmitter/sensor combination of FIG. 1.
Figure 11:
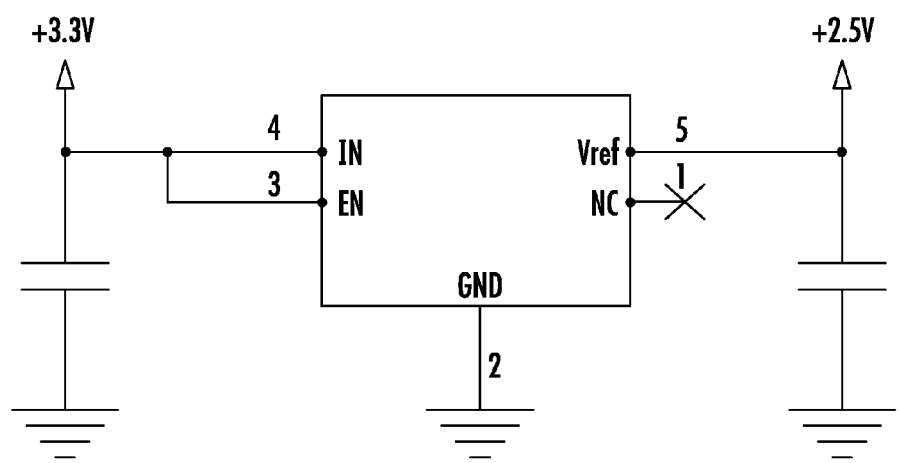
FIG. 11 is an exemplary circuit is shown for providing a reference voltage used by the transmitter processor.

Referring now to FIG. 10, an exemplary adjustable power supply ($V_{adjust}$ Output Voltage) circuit is shown. Referring to FIG. 11, an exemplary circuit is shown for providing a 2.5V reference voltage used by the transmitter processor 46. As previously noted, the transmitter processor compares the $V_{adjust}$ voltage reading from the sensor portion to this reference voltage to determines the need to adjust the $V_{adjust}$ voltage to the sensor portion.

Figure 12:
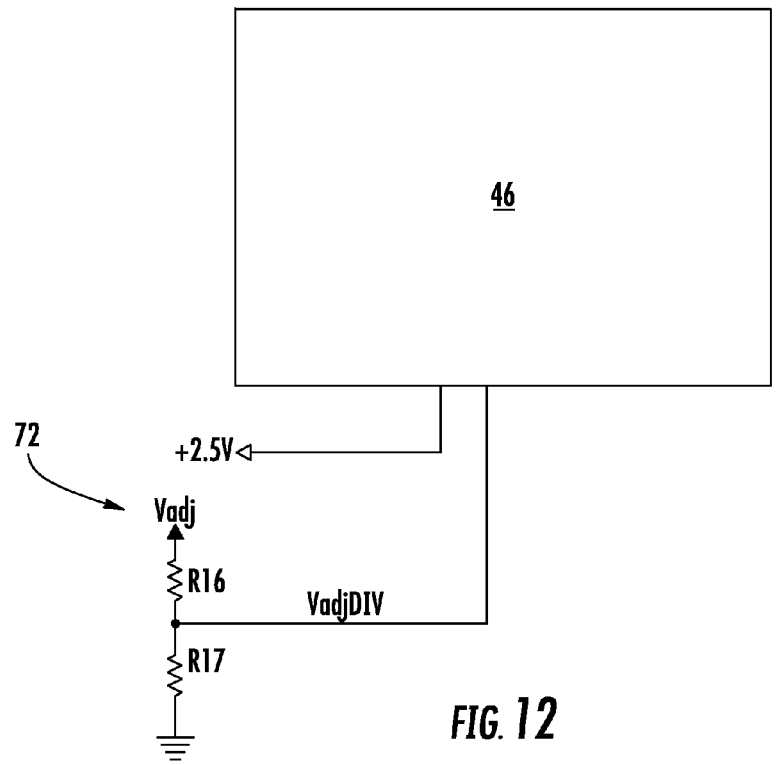
FIG. 12 is a schematic of an exemplary gas transmitter/sensor processor.
Figure 13:
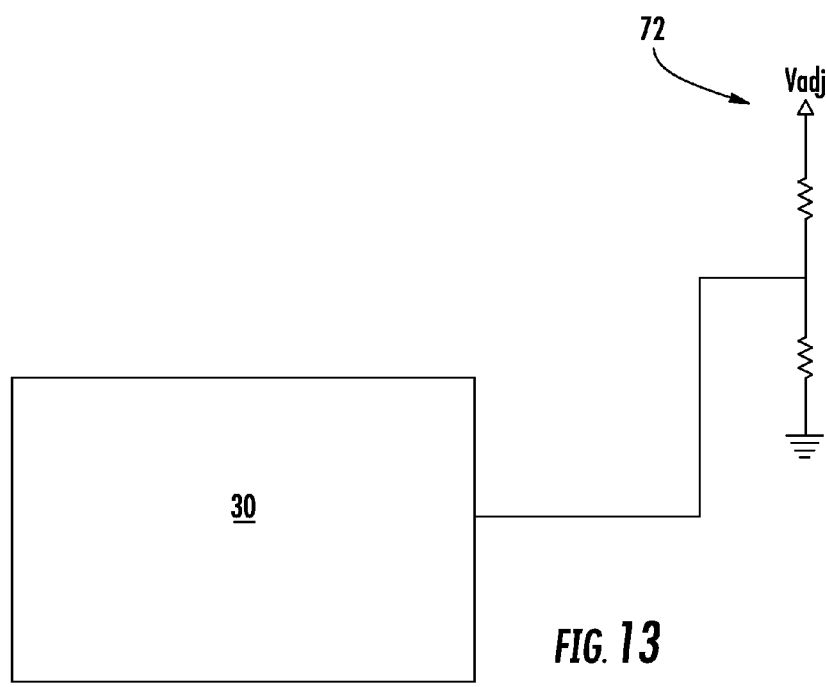
FIG. 13 is a schematic of an exemplary sensor processor.

Referring to FIG. 12, a schematic of an exemplary gas transmitter/sensor processor is shown in which $V_{adjust}$ output voltage is read through a voltage divider circuit and external reference voltage into the analog to digital (A/D) inputs. Referring to FIG. 13, a schematic of an exemplary sensor processor is shown in which $V_{adjust}$ output voltage is read through a voltage divider circuit into an analog to digital (A/D) inputs.

Thus described, the disclosed system may automatically adjust the excitation voltage provided to a particular sensor portion to match the exact requirements of the sensor type.

Thus, the specific voltage that a sensor requires may be different from a default voltage initially provided by the transmitter portion 4. The sensor-specific voltage may be stored as a parameter in the sensor's nonvolatile memory 62 and can be accessed by the sensor processor 30 and the transmitter processor 46. This parameter may be one of the parameters initially read by the transmitter portion 4 when it recognizes a new sensor portion 2 has been installed. The initial sensor voltage setting is read with an A/D converter on the processor board 36 of the transmitter portion 4. Once set, the transmitter processor 46 reads this voltage from the sensor portion 2 and uses that value as the initial voltage supplied to the sensor portion 2 by the transmitter portion 4.

To set this initial value, the transmitter processor 46 may set the first and second potentiometers 68, 70 to default values to provide the initial excitation voltage to the sensor portion 2. The sensor processor 30 measures the exact value of voltage received, and determines whether it corresponds to the voltage being provided by the transmitter portion 4. Both the transmitter and the sensor processors 46, 30 read the $V_{adjust}$ output voltage through a voltage divider circuit into an analog to digital (A/D) input on the respective processor (see FIGS. 12 and 13). The transmitter processor 46 uses an external reference voltage circuit for its measurements. The sensor processor 30 uses the internal voltage reference of the processor for its measurements. The sensor processor communicates to the transmitter processor the $V_{adjust}$ voltage reading at the sensor portion 2. The transmitter processor compares the $V_{adjust}$ voltage reading at the sensor portion 2 to the voltage reading at the transmitter processor 46 and determines the need to adjust the $V_{adjust}$ voltage to the sensor portion 2. If the transmitter processor 46 determines that a voltage adjustment is required, it adjusts the first and/or second potentiometer 68, 70 to provide the requisite adjusted voltage to the sensor portion 2.

In one embodiment, when a new sensor portion 2 is "plugged into" an associated transmitter portion 4, as part of an initialization process the sensor processor 30 communicates to the transmitter processor 46 that it requires an excitation voltage of, for example, 4.5 V. In response, the transmitter processor 46 adjusts the first and second potentiometers 68, 70 to provide 4.5 V to the sensor portion 2. The sensor begins operating, the sensor processor 30 measures the voltage actually received from the transmitter portion 4, and relays to the transmitter processor 46 the value of the actual received voltage. For example, although the transmitter portion may be configured to provide 4.5 V to the sensor portion, the actual voltage received by the sensor portion 2 may be 4.25 V, as measured at the sensor. When it receives this information from the sensor processor 30, the transmitter processor 46 may increase the voltage until the sensor senses 4.5 V.

Thus, the disclosed adjustable power supply arrangement is an automatic feature that "tells" the transmitter portion what excitation voltage the sensor portion is receiving, and provides closed loop error correction to ensure a desired voltage is being provided to the sensor portion at all times. In one embodiment, the circuitry of the adjustable power supply arrangement is provided as part of the transmitter portion 4, preferably as part of the processor board 36.

As will be appreciated, in addition to providing a correct initial voltage supply to the sensor portion 2, the disclosed power supply circuit can also automatically compensate for power supply voltage changes that result from local and environmental temperature changes.

Upon initial installation, sensors must to be calibrated. This requires a zeroing, which sets the zero offset in the sensor, as well as a spanning of the sensor, usually at 50% of full scale. This gives the sensor fixed points which are then used in calculating gas concentration. The disclosed system allows a sensor to be calibrated at a single value or limited range, followed by a re-ranging of the sensor and scaling of the calibration data so recalibration is not required for operation of the sensor in different ranges. For example, the system may read zero offsets at a new gain setting, compare to a previous zero offset, and then scale calibration factors by the same ratio in order to operate at a desired range.

The disclosed system and method may be used to provide replacement guidance for a particular sensor portion 2. Thus, during periodic sensor calibration operations, a corresponding loss of sensor sensitivity may be determined. This loss information can be trended over time to produce an end of life prediction. The trend information can also be used to adjust the gain parameters to extend the sensor's useful life. For example, the system may include a table of gain values for each range. A user may select from these gain values to obtain a desired operating range.

As previously noted, detection of different target gases requires the use of a variety of specific sensor types. In addition, to detect specific concentration ranges (e.g., 0-25 ppm, 0-50 ppm) of a target gas, specific signal conditioning must be provided to enable a transmitter to process the received signals. With current devices, such signal conditioning is provided by a sensor-specific or transmitter-specific conditioning circuit. This requires a large number of application specific sensors/transmitters to be stocked. The disclosed system and method eliminate the need for such application-specific circuits. With the disclosed system and method, by adjusting the gain built into the microprocessor instead of using fixed components, a single circuit type can be provided for a particular target gas. Using a gain adjustment, the sensing range (e.g., 0-25 ppm, 0-50 ppm) can be adjusted. The result is that only a single sensor need be stocked for a particular gas. In one embodiment, a sensor can be shipped using a default range, and the end user can adjust the sensor to one of a variety of pre-determined ranges via a user interface. For example, the transmitter processor may have a pair of operational amplifiers that can be arranged in a staged manner. Each amplifier may have a plurality of gain settings. In one non-limiting embodiment, each amplifier may have eight (8) gain settings. Thus, in combination, there would be 256 different combinations, but in practice many of the combinations could provide the same gain. A table of unique gain settings may be available to adjust the range. Based on the sensor's sensitivity and desired range, a gain value can be selected which optimizes the resolution in the A/D converter. These settings can be programmed into the sensor and made available to the user through a display menu. In some embodiments, discrete ranges would be made available, so a user would not have infinitely adjustable range scales.

Figure 14:
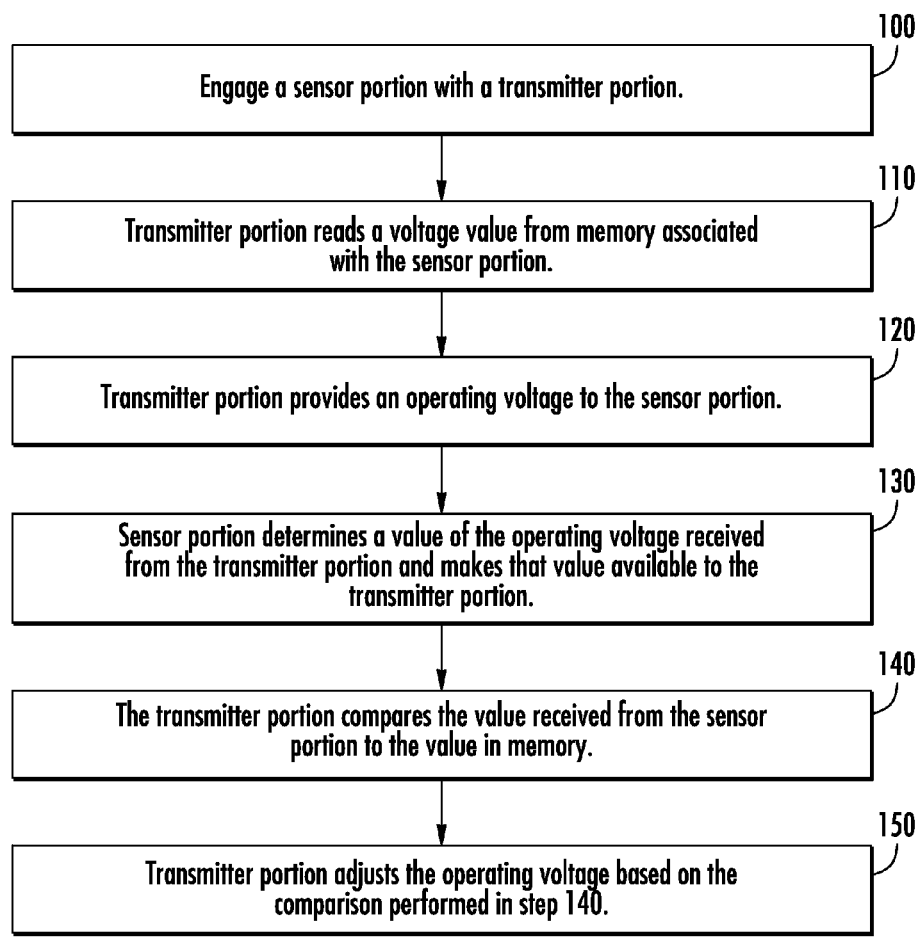
FIG. 14 is a flowchart illustrating an exemplary embodiment of the disclosed method.

Referring now to FIG. 14, a method according to one or more embodiments will be described. At step 100, a sensor portion 2 is engaged with a transmitter portion 4. At step 110, the transmitter portion 4 reads a voltage value from memory 62 associated with the sensor portion 2. At step 120, the transmitter portion 4 provides an operating voltage to the sensor portion. At step 130, the sensor portion 2 determines a value of the operating voltage received from the transmitter portion 4 and makes that value available to the transmitter portion 4. At step 140, the transmitter compares the value from the sensor portion 2 to the value in memory 62. At step 150, the transmitter portion 4 adjusts the operating voltage based on the comparison performed in step 140. In some embodiments, this adjustment is performed using a variable voltage supply. The variable voltage supply may include at least one potentiometer. In some embodiments, multiple potentiometers can be used to provide coarse and fine voltage adjustment.

Some embodiments of the disclosed device may be implemented, for example, using a storage medium, a computer-readable medium or an article of manufacture which may store an instruction or a set of instructions that, if executed by a machine, may cause the machine to perform a method and/or operations in accordance with embodiments of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for detecting the presence of a gas, comprising:
a transmitter portion including a transmitter processor;
a sensor portion including a sensor processor, the sensor portion adapted to sense gas; and
a variable voltage supply associated with the transmitter portion and the sensor portion, the variable voltage supply including a plurality of potentiometers to enable coarse and fine voltage adjustment;
the sensor processor configured to communicate a required voltage to the transmitter processor, the transmitter processor configured to set at least one of the plurality of potentiometers to a default value to deliver an operating voltage corresponding to the required voltage to the sensor portion, the sensor processor further configured to measure an actual voltage received from the transmitter processor and to communicate the actual voltage to the transmitter portion, the transmitter processor further configured to compare the actual voltage to the required voltage and to adjust the operating voltage toward the required voltage.

2. The system of claim 1, the transmitter portion for transmitting information received from the sensor portion to a wired or wireless network.

3. The system of claim 2, the transmitter portion configured to transmit an identity of at least one sensed gas, and a concentration of the at least one sensed gas.

4. A method for adjusting sensor excitation voltage, comprising:
a sensor portion of a gas sensing system communicating a required voltage to a transmitter portion of the gas sensing system;
providing, at the transmitter portion, an operating voltage corresponding to the required voltage to the sensor portion by setting at least one of a plurality of potentiometers of a variable voltage power supply to a default value;
measuring, at the sensor portion, an actual voltage;
receiving, at the transmitter portion, a signal from the sensor portion indicating the actual voltage;
comparing, at the transmitter portion, the actual voltage to the operating voltage; and
automatically adjusting, at the transmitter portion, the operating voltage toward the required voltage.

5. The method of claim 4, comprising transmitting information received from the sensor portion to a wired or wireless network.

6. The method of claim 5, wherein the transmitted information includes an identity of at least one sensed gas, and a concentration of the at least one sensed gas.

7. A universal gas sensor/transmitter unit, comprising:
a transmitter portion having a recess configured to engage a sensor portion adapted to sense gas, the transmitter portion including a transmitter processor and at least one power supply circuit for providing adjustable power to the sensor portion when the sensor portion is engaged with the recess of the transmitter portion, the power supply circuit including a first potentiometer for coarse voltage adjustment and a second potentiometer for fine voltage adjustment, the first and second potentiometers controllable by the transmitter processor to automatically adjust the power supplied to the sensor portion;
the sensor portion including a sensor processor configured to communicate a required voltage to the transmitter processor, the transmitter processor configured to set at least one of the first and second potentiometers to a default value to deliver an operating voltage corresponding to the required voltage to the sensor portion, the sensor processor further configured to measure an actual voltage received from the transmitter portion and to communicate the actual voltage to the transmitter processor, the transmitter processor further configured to compare the actual voltage to the required voltage and to adjust the operating voltage toward the required voltage.

8. The universal gas sensor/transmitter unit of claim 7, the sensor processor having an associated memory, the memory including a value representative of an excitation voltage of the sensor portion.

9. The universal gas sensor/transmitter of claim 8, the memory containing operational history information for the sensor portion.

10. The universal gas sensor/transmitter of claim 7, the external surface geometry of the sensor portion having a recess for receiving a seal member to seal the external surface geometry of the sensor portion to the recess of the transmitter portion.

* * * * *